United States Patent [19]

Rose et al.

[11] Patent Number: 5,019,422

[45] Date of Patent: May 28, 1991

[54] METHOD FOR PRODUCING A LIQUID IMPERMEABLE, GAS PERMEABLE FOAM BARRIER

[75] Inventors: Kenneth R. Rose; Martin M. Williams, both of Harrisburg, N.C.

[73] Assignee: Union Oil Company of California, Los Angeles, Calif.

[21] Appl. No.: 316,459

[22] Filed: Feb. 27, 1989

[51] Int. Cl.$^5$ .............................................. B05D 5/00
[52] U.S. Cl. ................................. 427/245; 427/369; 427/381; 427/393.4; 427/412
[58] Field of Search ............... 427/244, 245, 246, 369, 427/381, 393.4, 373, 387, 412; 428/314.2

[56] References Cited

U.S. PATENT DOCUMENTS

| | | | |
|---|---|---|---|
| 3,567,565 | 11/1967 | Jones et al. | 428/102 |
| 3,615,970 | 1/1969 | May | 156/78 |
| 3,713,868 | 1/1973 | Gordon et al. | 427/244 X |
| 3,862,291 | 1/1975 | Braudon, Jr. et al. | 428/314.2 X |
| 3,919,451 | 11/1975 | Levy et al. | 427/369 X |
| 4,146,027 | 3/1979 | Hoey | 428/314.2 X |
| 4,362,774 | 12/1982 | Brandon, Jr. et al. | 428/159 |
| 4,499,139 | 2/1985 | Schortmann | 428/245 |
| 4,761,326 | 8/1988 | Barnes et al. | 428/219 |

Primary Examiner—Evan Lawrence
Attorney, Agent, or Firm—Gregory F. Wirzbicki; Michael A. Kondzella

[57] ABSTRACT

A foam barrier system which is liquid impermeable and gas permeable is prepared by coating a polymeric, microporous foam upon a substrate, applying a composition having liquid repellency properties to the foam coated upon the substrate, and curing.

41 Claims, No Drawings

METHOD FOR PRODUCING A LIQUID IMPERMEABLE, GAS PERMEABLE FOAM BARRIER

FIELD OF THE INVENTION

This invention relates to the field of polymeric foams. In one of its more particular aspects, this invention relates to liquid impermeable foam barrier systems and to a method for producing foam barriers which are liquid impermeable and gas permeable.

BACKGROUND OF THE INVENTION

Polymeric, microporous foams have been applied to various fabrics and have found use, for example, as barriers to the passage of liquids and microorganisms. Where such barriers are applied to "breatheable" materials, that is, materials which are porous enough to permit the free circulation of air or other gases, it is important that the application of the barrier does not adversely affect the air permeability of the material to which the barrier is applied. Applications include protective garments for hospital and industrial uses, hospital drapes, fabric wraps for surgical instruments, backings for medical tapes and wound dressings, diapers, feminine hygiene products, adult incontinence products, rainwear, rain covers and tarpaulins. In hospital and medical/surgical applications, in particular, the use of foam-coated fabrics prevents the passage of water and other liquids such as blood, while permitting free flow of air. Their use prevents contamination by microorganisms such as bacteria or viruses, which may be present in various physiological fluids.

Free flow of air is critical in the case of medical tapes or wound dressings. While it is essential that wounds be kept sterile by excluding microorganisms from the wound, air should be permitted to contact the wound in order to keep it dry and promote healing. Breatheable fabrics are also needed in protective garments, since use of fabrics which are not breatheable may result in the wearer's discomfort and inconvenience due to excessive perspiration, which cannot evaporate through the fabric by the circulation of air, unless the fabric is breatheable.

Foam-coated fabrics have achieved wide use because they are economical, comfortable, drapeable, nonlinting, heat-sealable, and sterilizable by steam, gas or gamma radiation. In addition, foam-coated fabrics can be made antistatic, antimicrobial, or flame retardant or can have other desirable properties imparted to them by appropriate treatment.

In U.S. Pat. No. 3,567,565, R. L. Jones et al. disclosed a laminate having increased strength and dimensional stability. The laminate consists of a foam laminated to a warp knitted fabric.

In U.S. Pat. No. 3,615,970, R. E. May disclosed foam-laminated glass fabrics, in which the latex which is foamed contains a flame retardant plasticizer.

In U.S. Pat. No. 4,499,139, W. E. Schortmann described the use of a froth sizing to establish a bacterial barrier in fabrics used in surgical gowns. The sizing is worked below the surface of the fabric and leaves the outer surface of the fabric froth-free.

SUMMARY OF THE INVENTION

In accordance with the present invention, a liquid-impermeable, gas-permeable, microporous, polymeric foam barrier is provided. The barrier is especially useful in the production of barrier systems constituting breatheable, water-impermeable, nonwoven fabrics. It is prepared by a process which includes the steps of introducing a gas into a polymeric latex to produce a foam; applying the foam to a substrate; drying the foam upon the substrate; applying a water repellent to the dried foam; and curing. The resulting microporous, polymeric foam is impermeable to liquids and permeable to gases. It is particularly effective in providing protection against moisture, body fluids, and microorganisms and is adaptable to any use in which it is desired to have a water repellent barrier comprised of a "breatheable" material.

DETAILED DESCRIPTION OF THE INVENTION

The liquid impermeable, gas permeable, microporous, polymeric foam barrier of the present invention is usually formed upon a fabric substrate, preferably a nonwoven fabric substrate, to produce a foam barrier system. While any knitted or woven fabric can be used, if desired, it is generally advantageous to use nonwoven fabrics because of the economy inherent in their use. Among nonwoven substrates which can be used are air and wet laid substrates, carded substrates, spunbonded substrates, and hydroentangled or spunlaced substrates.

The foam coating, which is usually applied without any surface treatment of the substrate, is prepared by aerating or otherwise foaming an aqueous polymeric formulation to the density desired. The polymeric formulation will generally contain a polymer dispersion or latex. Other materials can be included in the formulation depending upon the use for which the foam-coated fabric or barrier system is intended.

Suitable latexes include, for example, acrylic latexes, vinyl acrylic latexes, styrene-butadiene latexes, vinyl chloride latexes, vinyl acetate latexes, vinylidene chloride latexes, nitrile latexes, and urethane latexes. Latexes comprised of copolymers formed by the copolymerization of the monomers utilized in the latexes mentioned above with other monomers copolymerizable with such monomers can also be used.

The polymeric formulation can also contain fillers and foam aids, such as surfactants and foam stabilizers. In addition, the use of colorants, thickeners, cross-linkers and various special ingredients such as antistatic agents, antimicrobial agents and flame retardants, for example, is optional.

Fillers which can be used include clays, titanium dioxide, talc, feldspar, pyrophyllite, alumina and calcium carbonate. Other filler materials which contribute to the properties desired of the foam-coated fabric can be used as well. In some cases no filler will be used. The filler loading is typically from about 0 to about 400 parts per hundred parts dry latex. Particularly preferred is a filler loading of about 140 to about 170 parts filler per 100 parts dry latex and especially about 160 parts filler per 100 parts dry latex.

In order to produce a foam coating having the desired properties, that is, a distinctive microporous cellular structure with interconnecting cells and a high level of heat stability, the formulation including latex, fillers, foam aids stabilizers and other special ingredients, if desired, is foamed or aerated to a blow ratio of about 5 to 1 to about 20 to 1 and preferably about 8 to 1 to about 10 to 1. Blow ratio is defined as the ratio of parts of air to parts of liquid and determines the foam density.

Foaming can be accomplished using any conventional industrial or laboratory equipment, for example, an Oakes foamer, a Texilease foamer, a Hobart mixer, a Kitchen-Aid mixer or a hand mixer.

The foam having the desired density is then coated onto the substrate. Coating can be accomplished using any suitable coating method which will give the desired coat weight or add-on. For example, a Gardner knife, rod coater or similer means can be used for this purpose. The foam is coated onto the substrate to the thickness desired for the particular application for which the foam barrier system is intended. In general, the foam is coated to an extent of about 0.1 to 1 ounce per square yard of substrate and preferably about 0.25 to 0.75 ounce per square yard of substrate.

After the foam has been applied to the substrate in the desired quantity, the foam is dried at an elevated temperature. The foam can be dried within the temperature range of about 200° to 325° F. and crushed between nip rollers at pressures of about 10 to 80 psi. The higher the temperature the less time will be required for drying. Preferably the foam is dried at 250° F. for about 2 minutes and crushed at a pressure of about 40 psi.

The resulting dried foam is at least somewhat hydrophilic, which enables the efficient and uniform absorption of various materials having special properties, for example, a composition capable of imparting the property of water repellency to the foam-coated fabric.

In the present invention, a water repellent is introduced into the foam barrier. This can be accomplished in three general ways:

(1) The water repellent can be applied to the polymeric foam coated upon the substrate following drying as described above, after which the foam containing the water repellent is subjected to an elevated temperature for curing.

It has been found that application of the water repellent is best effected by padding onto the foam-coated fabric. Padding is the process of dipping or saturating the substrate in a bath and squeezing off the excess liquid with nip rollers.

(2) The water repellent can itself be applied as a foam over the dried polymeric foam, following which it is subjected to an elevated temperature for curing.

(3) The water repellent can be applied to the wet polymeric foam for example, by padding, after which it is subjected to an elevated temperature for curing.

Various water repellents can be used. Typical of these are aqueous fluoropolymer dispersions such as Scotchban FC-824, FC-831, FC-834 and FC-461, available from 3M Company, St. Paul, Minn., and Zonyl NWG, Zonyl NWF, Zepel RS and Zepel RN, available from DuPont Company, Wilmington, Del. It is also possible to utilize a wax dispersion or a wax extender such as Aerosol 96, available from American Cyanamid Company, Wayne, N.J., either alone or preferably in combination with the fluoropolymer dispersion mentioned above. Application to the foam-coated substrate, in embodiments (1) and (3) above, can be accomplished by use of a padding bath having a concentration of about 1 percent to about 5 percent, by weight, and preferably about 2.5 percent to about 3 percent, by weight, in the case of the fluoropolymers and a concentration of about 1 percent to about 10 percent, by weight, in the case of the waxes. A wet pick-up of about 30 percent to about 90 percent is desired, preferably about 50 percent to about 80 percent. Percent wet pick-up is defined as the weight of the liquid absorbed divided by the initial weight of the substrate times 100.

Although padding is the preferred method of application of the water repellent, the water repellent can be applied to the foam-coated substrate as a foam as indicated in embodiment (2) above. One advantage of foaming the water repellent rather than padding it upon the foam-coated substrate is that the air present in the foam facilitates drying with less expenditure of energy.

Following application of the water repellent, the water repellent-treated foam-coated substrate is dried and cured at an elevated temperature. In general, temperatures higher than those for drying, as described above, and preferably of at least about 300° F. and cure times of at least about 2 minutes are desired. However, if a temperature-sensitive substrate is used, it is desirable to cure at a somewhat lower temperature, for example, at a temperature of about 275° F. or below to prevent distortion of the substrate. Foams coated on temperature-sensitive substrates are typically cured for about 2 to 5 minutes at temperatures of about 240° to 275° F. and preferably for about 3 minutes at about 250° F.

Although the invention has been described with respect to a preferred embodiment in which the foam-coated substrate is dried prior to application of the water repellent, it is possible to apply the water repellent to the foam-coated substrate without prior drying of the foam and to then cure the water repellent-treated foam-coated substrate. This variation has the advantage of subjecting the foam-coated substrate to elevated temperatures but once, rather than once upon drying the foam-coated substrate and a second time upon curing after application of the water repellent.

The invention is further described in the following examples which are illustrative of specific modes of practicing the invention and are not intended as limiting the scope of the invention as defined by the claims. All percentages are by weight unless otherwise specified.

In the following examples, foam-coated samples were evaluated with respect to water repellency by means of two standard tests, the Mason Jar Test and the Impact Penetration Test. The Mason Jar Test is outlined in the International Nonwovens and Disposables Association (INDA) Test Method IST 80.7-70. In this test, a piece of sample fabric is placed over the mouth of a Mason jar containing 600 ml of a 0.9 percent saline solution. The jar is inverted and placed on a glass plate and the time until the sample leaks is recorded. The Impact Penetration Test is outlined in the American Association of Textile Chemists and Colorists (AATCC) Test Method 42-1974. In this test 500 ml of water are sprayed from a height of 2 feet onto the test specimen, which is backed by a piece of weighed blotter paper. The blotter paper is reweighed following spraying to determine the amount of water penetration and the difference in weights is reported in grams.

The following example illustrates a preferred embodiment of the present invention.

EXAMPLE 1

A styrene butadiene-based latex formulation was prepared using the recipe shown in Table 1.

TABLE 1

| Ingredient | Solids, % | Dry, % | Wet, % |
|---|---|---|---|
| Latex[1] | 50 | 29.0 | 58.0 |
| H$_2$O | — | — | 21.0 |
| Clay Slurry | 67 | 43.5 | 65.0 |

TABLE 1-continued

| Ingredient | Solids, % | Dry, % | Wet, % |
|---|---|---|---|
| Titanium Dioxide Slurry | 78 | 3.0 | 3.8 |
| Surfactant[2] | 35 | 0.5 | 1.4 |
| Thickening Agent[3] | 20 | 0.25 | 1.25 |
| Aqua Ammonia | — | — | 0.38 |
| Ammonium Stearate | 34 | 1.50 | 4.4 |
| | | 77.75 | 155.23 |

[1]76 RES 5550, a carboxylated SBR copolymer latex available from UNOCAL Chemical Division, Union Oil Company of California, Los Angeles, California.
[2]Aerosol 18, an N-alkylsulfosuccinamate, available from American Cyanamid Co., Wayne, New Jersey.
[3]Acrysol ASE-95, a polyacrylate thickener, available from Rohm and Haas Co., Philadelphia, Pennsylvania.

Two hundred grams of the formulation of Table 1, having a viscosity of 1200 cps (Brookfield Viscometer LVT, No. 4 Spindle at 60 rpm) at pH 9.5, were foamed at high speed in a Kitchen Aid mixer to a blow ratio of 8 to 1. The foam was refined by mixing on low speed for several minutes and then coated onto a 2.25 oz/yd$^2$ pulp nonwoven substrate using a Gardner knife. The coating was dried in a forced air oven for 2 minutes at 250° F. and crushed using nip rollers at 40 psi, and the dry foam add-on was determined to be approximately 0.3 oz/yd$^2$. The sample was padded using a bath containing 3 percent Scotchban FC 824 aqueous fluoropolymer dispersion. A 70 percent wet pick-up was obtained. The sample was cured for 2 minutes at 300° F. and then tested for water repellency by the Mason Jar and Impact Penetration tests. The test sample had a Mason Jar value of >3 hours and an Impact Penetration of <0.1 gram.

The following example illustrates the effect of omitting the foam coating of the present invention and using only a water repellent.

EXAMPLE 2

The 2.25 oz/yd$^2$ pulp nonwoven substrate of Example 1 without any coating was padded with a solution containing 4 percent Scotchban FC 824 aqueous fluoropolymer dispersion and 12.5 percent Aerosol 96 wax extender. The wet pick-up was 70 percent. The sample was dried and tested for water repellency by the Mason Jar and Impact Penetration tests. The sample had a Mason Jar Test value of >3 hours and an Impact Penetration test value of 16.8 grams.

The foregoing example demonstrates the importance of the microporous foam of the present invention in obtaining superior water impermeability, since the Impact Penetration Test value was unacceptably higher than that obtainable according to the present invention, as shown in Example 1.

The following example illustrates the effect of incorporating the water repellent into the latex formulation prior to foaming.

EXAMPLE 3

The water repellent of Examples 1 and 2 was post-added to the latex formulation of Example 1. The latex formulation containing the water repellent was then foamed and coated onto the pulp substrate of Example 1 to an add-on level of 0.3 oz/yd$^2$. The amount of water repellent used was 15 grams per 100 grams of latex formulation, which represented a level of water repellent twice that used in Example 1. The sample was evaluated for Mason Jar and Impact Penetration performance. The sample gave a Mason Jar Test value of approximately 20 minutes and an Impact Penetration value of 10.2 grams.

As demonstrated by the results obtained in Example 3, the technique of applying the water repellent onto the foam-coated substrate, in accordance with the present invention, results in a product which is superior to that obtained by adding the water repellent to the latex formulation prior to foaming.

The following example illustrates the use of an acrylic latex and an optional method of crushing the foam in the preparation of a foam barrier in accordance with the present invention.

EXAMPLE 4

An acrylic-based latex formulation was prepared using the recipe shown in Table 2.

TABLE 2

| Ingredient | Solids, % | Dry, % | Wet, % |
|---|---|---|---|
| Latex[1] | 49 | 231.9 | 473.2 |
| H$_2$O | — | — | 165.0 |
| Clay Slurry | 67 | 348.4 | 520.0 |
| Titanium Dioxide Slurry | 78 | 23.7 | 30.4 |
| Surfactant[2] | 35 | 4.3 | 12.3 |
| Aqua Ammonia | — | — | 6.2 |
| Cross-linker[3] | 85 | 6.8 | 8.0 |
| Ammonium Stearate | 34 | 13.5 | 39.8 |
| Ammonium Chloride | 20 | 1.5 | 7.5 |
| | | 630.1 | 1262.4 |

[1]76 RES 2131, an acrylic copolymer latex, available from UNOCAL Chemical Division, Union Oil Company of California, Los Angeles, California.
[2]Aerosol 18
[3]Cymel 303, a methoxymethyl melamine cross-linking agent, available from American Cyanamid Co., Wayne, New Jersey.

Two hundred grams of the formulation of Table 2 were foamed at a blow ratio of 8 to 1 and coated onto a 2.25 oz/yd$^2$ pulp substrate to an add-on of 0.3 oz/yd. The foam-coated substrate was dried for 2 minutes. at 250° F. The foam-coated substrate was then padded with a solution containing 2.5 percent Scotchban FC 824 aqueous fluoropolymer dispersion and 6.5 percent Aerosol 96 wax extender. A 70 percent wet pick-up was obtained. The resulting treated foam-coated substrate was wet crushed and then cured for 2 minutes at 300° F. The sample was evaluated for water repellency and gave a Mason Jar value of >3 hours and an Impact Penetration Test value of <0.1 gram.

The following example illustrates the use of a spunbonded polypropylene substrate in preparing a foam barrier in accordance with the present invention.

EXAMPLE 5

The latex formulation of Example 4 was foamed and applied to a 1.5 oz/yd$^2$ spunbonded polypropylene substrate to an add-on of 0.5 oz/yd$^2$. The foam-coated substrate was dried, padded with the water repellent of Example 4, crushed and cured as described in Example 4 and then evaluated for water repellency. The sample gave a Mason Jar Test value of >3 hours and an Impact Penetration test value of <0.1 gram.

The following example illustrates the use of a spunlaced nonwoven substrate in preparing a foam barrier in accordance with the present invention.

EXAMPLE 6

The latex formulation of Example 4 was foamed to a blow ratio of 8 to 1 and applied to a 1.85 oz/yd$^2$ spunlaced nonwoven substrate to an add-on level of 0.43 oz/yd$^2$. The foam-coated substrate was dried, padded with the water repellent of Example 4, crushed and cured as described in Example 4 and then evaluated for water repellency. The sample gave a Mason Jar Test value of >3 hours and an Impact Penetration Test value of 0 grams.

This invention may be embodied in other forms without departure from the spirit or essential characteristics thereof. For example, it is recognized that, while the description of the present invention and the preferred embodiments thereof are directed toward foam barriers utilizing nonwoven fabrics, there may be applications wherein it is desirable to utilize a woven or knitted substrate. Consequently, the present embodiment and examples are considered only as being illustrative and not restrictive, with the scope of the invention being indicated by the appended claims. All embodiments which come within the scope and equivalency of the claims are, therefore, intended to be embraced therein.

We claim:

1. A process for producing a liquid impermeable, gas permeable, microporous, polymeric foam barrier system which comprises the steps of:
   introducing a gas into a polymeric latex to form a gas permeable microporous foam;
   applying said foam to a substrate;
   drying the foam upon said substrate;
   applying to the dried foam a composition for imparting liquid repellency thereto; and
   curing the resulting foam barrier system by subjecting the resulting foam barrier system to an elevated temperature.

2. A process according to claim 1 wherein said gas is air.

3. A process according to claim 1 wherein said gas is introduced to a blow ratio of about 5 to 1 to about 20 to 1.

4. A process according to claim 1 wherein said gas is introduced to a blow ratio of about 8 to 1 to about 10 to 1.

5. A process according to claim 1 wherein said gas is introduced to a blow ratio of about 8 to 1.

6. A process according to claim 1 wherein said polymeric latex is an acrylic latex.

7. A process according to claim 1 wherein said polymeric latex is a vinyl acrylic latex.

8. A process according to claim 1 wherein said polymeric latex is a styrene-butadiene latex.

9. A process according to claim 1 wherein said polymeric latex is a vinyl chloride latex.

10. A process according to claim 1 wherein said polymeric latex is a vinyl acetate latex.

11. A process according to claim 1 wherein said polymeric latex is a vinylidene chloride latex.

12. A process according to claim 1 wherein said polymeric latex is a nitrile latex.

13. A process according to claim 1 wherein said polymeric latex is a urethane latex.

14. A process according to claim 1 wherein said polymeric latex is a latex comprised of the product of the copolymerization of the monomers utilized in a latex selected from the group consisting of arylic latexes, vinyl acrylic latexes, styrene-butadiene latexes, vinyl chloride latexes, vinyl acetate latexes, vinylidene chloride latexes, nitrile latexes, and urethane latexes, with a monomer copolymerizable therewith.

15. A process according to claim 1 wherein a filler is added to said polymeric latex and the filler loading is about 0 to about 300 parts per hundred parts dry latex.

16. A process according to claim 1 wherein a filler is added to said polymeric latex and the filler loading is about 140 parts to about 170 parts per hundred parts dry latex.

17. A process according to claim 1 wherein a filler is added to said polymeric latex and the filler loading is about 160 parts per hundred parts dry latex.

18. A process according to claim 1 wherein a surfactant is added to said polymeric latex.

19. A process according to claim 1 wherein a foam stabilizer is added to said polymeric latex.

20. A process according to claim 1 wherein a member selected from the group consisting of colorants, thickeners, cross-linkers, antistatic agents, antimicrobial agents and flame retardants is added to said polymeric latex.

21. A process according to claim 1 wherein said substrate is a fabric selected from the group consisting of knitted, woven and nonwoven fabrics 22. A process according to claim 1 wherein said substrate is a nonwoven fabric selected from the group consisting of air and wet laid substrates, carded substrates, spunbonded substrates, and hydroentangled or spunlaced substrates.

23. A process according to claim 1 wherein said foam is applied to said substrate in a quantity of about 0.1 to about 1 ounce per square yard.

24. A process according to claim 1 wherein said foam is applied to said substrate in a quantity of about 0.25 to about 0.75 ounce per square yard.

25. A process according to claim 1 wherein said foam is dried at a temperature of about 250° F. to about 300° F. for about 2 minutes.

26. A process according to claim 1 wherein said foam is dried at a temperature of about 250° F. to about 300° F. for about 2 minutes and crushed.

27. A process according to claim 1 wherein said composition for imparting liquid repellency is an aqueous fluoropolymer dispersion.

28. A process according to claim 1 wherein said composition for imparting liquid repellency is a wax extender.

29. A process according to claim 1 wherein said composition for imparting liquid repellency is a mixture of an aqueous fluoropolymer dispersion and a wax extender.

30. A process according to claim 2 wherein said composition for imparting liquid repellency is applied by passing from a bath having a concentration of said composition of about 1 to about 10 percent, by weight.

31. A process according to claim 1 wherein said composition for imparting liquid repellency is an aqueous fluoropolymer dispersion applied by padding from a bath having a concentration of said composition of about 1 to about 5 percent, by weight.

32. A process according to claim 1 wherein said composition for imparting liquid repellency is applied by padding from a bath containing an aqueous fluoropolymer dispersion in a concentration of about 2.5 to about 3 percent, by weight, and a wax extender in a concentration of about 1 to about 10 percent, by weight.

33. A process according to claim 1 wherein said composition for imparting liquid repellency is a water repellent.

34. A process according to claim 1 wherein said composition for imparting liquid repellency is absorbed to to the extent of about 30 to about 90 percent wet pick-up.

35. A process according to claim 11 wherein said composition for imparting liquid repellency is absorbed to the extent of about 50 to about 80 percent wet pickup.

36. A process according to claim 11 wherein said foam to which has been applied said composition for imparting liquid repellency is cured at a temperature of about 275° F. to about 300° F. for about 2 minutes.

37. A process according to claim 1 wherein said substrate having said foam barrier formed thereon has a Mason Jar Test value of >3 hours and an Impact Penetration Test value of <0.1 gram.

38. A process for producing a liquid impermeable, gas impermeable, microporous, polymeric foam barrier system which comprises the steps of:
    introducing a gas into a polymeric latex to form a gas permeable microporous foam;
    applying said foam to a substrate;
    applying to said foam a composition for imparting liquid repellency thereto; and
    curing the resulting foam barrier system by subjecting the resulting foam barrier system to an elevated temperature.

39. A process according to claim 38 wherein said foam is crushed following application of said composition for imparting liquid repellency thereto and prior to subjecting the resulting foam barrier system to an elevated temperature.

40. A process according to claim 38 wherein said foam is crushed following subjecting the resulting foam barrier system to an elevated temperature.

41. A process according to claim 38 wherein said composition for imparting liquid repellency is a water repellent.

* * * * *